United States Patent [19]

Garrou et al.

[11] 4,262,147
[45] * Apr. 14, 1981

[54] HYDROFORMYLATION OF DICYCLOPENTADIENE TO ITS DIMETHANOLIC DERIVATIVES

[75] Inventors: Philip E. Garrou, Holliston, Mass.; George E. Hartwell, Midland, Mich.

[73] Assignee: The Dow Chemical Company, Midland, Mich.

[*] Notice: The portion of the term of this patent subsequent to Apr. 8, 1997, has been disclaimed.

[21] Appl. No.: 21,145

[22] Filed: Mar. 16, 1979

Related U.S. Application Data

[63] Continuation-in-part of Ser. No. 873,314, Jan. 30, 1978, abandoned.

[51] Int. Cl.³ .................................................. C07C 29/16
[52] U.S. Cl. ..................................... 568/817; 568/909
[58] Field of Search ................................ 568/817, 909

[56] References Cited

U.S. PATENT DOCUMENTS

| | | | |
|---|---|---|---|
| 2,841,614 | 7/1958 | Buchner et al. | 568/817 X |
| 2,850,536 | 9/1958 | Buchner et al. | 568/817 |
| 2,875,244 | 2/1959 | Bartlett et al. | 568/817 X |
| 2,880,241 | 3/1959 | Hughes | 568/817 |
| 2,881,208 | 4/1959 | Buchner et al. | 568/817 X |
| 4,144,191 | 3/1979 | Hartwell et al. | 568/909 X |

*Primary Examiner*—Bernard Helfin
*Attorney, Agent, or Firm*—Charles Enright

[57] ABSTRACT

Dicyclopentadiene is selectively and substantially hydroformylated to its dimethanolic derivatives by a process comprising contacting dicyclopentadiene with a gaseous mixture of carbon monoxide and hydrogen at a temperature of at least about 100° C. and a pressure of at least about 1,000 psig in the presence of a catalytic amount of a catalyst consisting essentially of a rhodium-cobalt bimetallic cluster, such as $Rh_2Co_2CO_{12}$, supported on an amine resin, such as DOWEX ® MWA-1.

10 Claims, No Drawings

HYDROFORMYLATION OF DICYCLOPENTADIENE TO ITS DIMETHANOLIC DERIVATIVES

CROSS-REFERENCE TO RELATED APPLICATION

This application is a continuation-in-part of U.S. patent application, Ser. No. 873,314, filed Jan. 30, 1978 and now abandoned.

BACKGROUND OF THE INVENTION

1. Field of the Invention

This invention relates to dicyclopentadiene (DCPD), catalytic amine resin-supported rhodium-cobalt bimetallic clusters, and a hydroformylation process for preparing diols from nonconjugated dienes.

2. Description of the Prior Art.

The dimethanolic derivatives of DCPD (I)

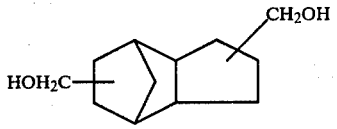

are useful compounds in the manufacture of polyester and polycarbonate compositions. These derivatives can be prepared by any one of a number of different processes. For example, Buchner et al., U.S. Pat. No. 2,850,536, teach a two-step process comprising first adding water gas to DCPD in the presence of diluting agents, polymerization inhibitors, stabilizers and a cobalt carbonyl catalyst to produce DCPD dialdehydes and second, hydrogenating the dialdehydes to the corresponding DCPD dimethanols. Falbe, Can. Pat. No. 893,716, teaches a similar two-step process except his process uses a rhodium-containing catalyst rather than a cobalt carbonyl catalyst and it does not employ polymerization inhibitors and stabilizers.

While both these and other exemplary processes demonstrate utility, each have certain undesirable features. First, each is a two-step process. Second, each commences with purified DCPD, i.e., DCPD containing less than about 5 weight percent impurities. Third, Buchner et al. report relatively poor (about 50 weight percent) selectivity while Falbe reports relatively severe (typically about 130° C. and 3,000 psig) hydroformylation conditions. These features detract generally from the overall efficiency of these processes.

Applicants' copending application entitled "Amine-Resin Supported Rhodium-Cobalt Bimetallic Clusters as Novel Hydroformylation Catalysts", Ser. No. 803,815, filed June 6, 1977, describes the title compounds, a method for their preparation, and a hydroformylation process for their use.

SUMMARY OF THE INVENTION

According to this invention, dimethanolic derivatives of DCPD, I, are efficiently prepared by a process comprising contacting DCPD with a gaseous mixture of carbon monoxide and hydrogen at a temperature of at least about 100° C. and a pressure of at least about 1,000 psig in the presence of a catalytic amount of a catalyst consisting essentially of a rhodium-cobalt bimetallic cluster supported on an amine resin. This process can utilize both purified and crude DCPD and it can also produce a product from either DCPD which is suitable for direct (i.e., without prior purification) use in the manufacture of polyesters and polycarbonates. Moreover, the process demonstrates exceptionally good yields of and selectivity for the dimethanolic (as compared to monomethanolic or hydrogenated) derivatives of DCPD.

DETAILED DESCRIPTION OF THE INVENTION

"Dicyclopentadiene (DCPD)" as here used includes both crude and purified DCPD. Crude DCPD is a hydrocarbon stream, such as that taken from a naphtha or LPG cracker, comprising at least about 50 and generally not in excess of about 95 weight percent DCPD. Other components of crude DCPD typically include: lights, such as benzene, $C_4$ olefins, etc.; $C_9$ and $C_{10}$ codimers, such as the codimers of butadiene and DCPD, isoprene and DCPD, etc.; isoprene dimer; $C_{11}$ codimers, such as the codimers of $C_6$ olefins and DCPD, etc.; olefins of 12 or more carbon atoms; and nonhydrocarbon material, such as oxygenated hydrocarbons, sulfur and nitrogen compounds, etc. Preferably, the crude DCPD of this invention comprises at least about 70 weight percent, and more preferably about 80 weight percent, DCPD with only minor (generally less than about 3 weight percent) amounts of olefins of 12 or more carbon atoms and negligible (generally less than about 0.5 weight percent) amounts of nonhydrocarbon material. Typically, crude DCPD does not comprise in excess of 90 weight percent DCPD. Both endo and exo DCPD isomers are generally present in crude DCPD but the endo isomer usually greatly predominates. Illustrative, preferred crude DCPD, such as that taken from a naphtha cracker, comprises between about:

| Component | Wt. % |
| --- | --- |
| Lights | 4–6 |
| $C_9$ and $C_{10}$ codimers | 12–18 |
| Isoprene dimer | 2–3 |
| exo-DCPD | 0.5–1 |
| endo-DCPD | 75–80 |
| $C_{11}$ dimers | 1–2 |
| >$C_{12}$ olefins | <1 |
| Nonhydrocarbon material | <0.5 |

The $C_9$ and $C_{10}$ codimers, isoprene dimer, exo- and endo-dicyclopentadiene and $C_{11}$ dimers are nonconjugated dienes.

Purified DCPD is DCPD comprising 5 or less weight percent of impurities, i.e., material other than DCPD. Typically, purified DCPD is crude DCPD upgraded to comprising at least about 95 weight percent DCPD. However, purified DCPD also includes DCPD obtained from sources other than crude DCPD, such as from the dimerization of purified cyclopentadiene. Purified DCPD can be comprised of either or both the endo- and exo-DCPD isomers.

The supported catalysts here used are generally prepared by loading onto an amine resin a bimetallic cluster of the formula:

$$Rh_xCO_yCO_{12} \qquad (II)$$

wherein x and y are individually integers of 1–3 with the proviso that $\Sigma(x+y)=4$. These bimetallic clusters are tetranuclear carbonyls and are readily synthesized by any number of varying methods. For example, tetranuclear carbonyl $Rh_2Co_2(CO)_{12}$ can be prepared by either of the following methods (III, IV):

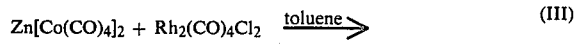

$$Zn[Co(CO)_4]_2 + Rh_2(CO)_4Cl_2 \xrightarrow{toluene} Rh_2Co_2(CO)_{12} + ZnCl_2 \quad (III)$$

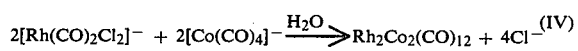

$$2[Rh(CO)_2Cl_2]^- + 2[Co(CO)_4]^- \xrightarrow{H_2O} Rh_2Co_2(CO)_{12} + 4Cl^- \quad (IV)$$

These and other methods for preparing the bimetallic clusters of this invention are further described by Martinengo et al., *J. Organometal. Chem.*, 59, 379 (1973). Conventional methods for preparing the monometallic carbonyls, e.g., $Zn[Co(CO)_4]_2$, etc., are described by King, *Organometallic Synthesis*, 1, 98–101 (1965). Clusters wherein x and y are each 2 are preferred.

Any amine resin that can be loaded with the bimetallic cluster (II) can be used in the practice of this invention. These resins are typically cross-linked and essentially water-insoluble, and they comprise primary, secondary and/or tertiary integral and/or pendant amine functionality. By "integral" amine functionality is meant that the amine functionality, i.e., amino group, is incorporated directly into the resin matrix. Examples of such resins include: polyethylenepolyamine cross-linked with epichlorohydrin, urea-formaldehyde cross-linked copolymers, melamine-formaldehyde cross-linked copolymers, etc. By "pendant" amine functionality is meant that the amine functionality is suspended from the resin matrix (backbone). This resin backbone can be varied to convenience and can comprise essentially any cross-linked compositions, such as styrene-divinyl-benzene, styrene-glycoldimethacrylate, aniline-formadehyde, aryl/polyamine-formaldehyde, phenol-formaldehyde, polyacrylate, etc. The pendant amine functionality can also vary to convenience and includes such diverse functionality as primary, secondary and tertiary amines, di-, tri- and polyamines, hydrolyzed oxazolines, etc. Examples of such resins, all commercially available and described generally as weak-base anion exchange resins, include: DOWEX ® MWA-1, WGR and 44 (manufactured by The Dow Chemical Company); Amberlite ® IRA-45, 68 and 93 (manufactured by Rohm & Haas Company); Duolite ® A-7 and A-14 (manufactured by Diamond Alkali Company); and Ionac ® A-260 (manufactured by Ionac Chemical Corporation).

The amine resins of this invention can take many forms, but swellable gel or macroporous beads are the most common and are thus preferred. Resins having pendant amine functionality are preferred to resins having integral amine functionality and resins having an exchange capacity of at least about 3 milliequivalents per gram of dry resin are particularly preferred. These latter resins include resins comprising a cross-linked polymer matrix having pendant amine functionality of the formulae —N(R)$_2$ and/or —NHR'N(R)$_2$ wherein each R is individually hydrogen or C$_1$–C$_6$ alkyl, R' is C$_2$–C$_6$ alkylene, and the open valence is the bond that joins the functionality to the polymer matrix. Typical substituents include: R alkyls, such as methyl, ethyl, propyl, isopropyl, butyl, etc.; and R' alkylenes, such as ethylene, propylene, hexylene, etc. The radical —NHR'N(R)$_2$ represents various diamines and alkyl-substituted diamines such as:

| —NHR'N(R)$_2$ | R' | N(R)$_2$ |
|---|---|---|
| ethylenediamine | —CH$_2$CH$_2$— | NH$_2$ |
| propylenediamine | —CH$_2$CH$_2$CH$_2$— | NH$_2$ |
| hexylenediamine | —CH$_2$(CH$_2$)$_4$CH$_2$— | NH$_2$ |
| N-methylethylenediamine | —CH$_2$CH$_2$— | NHCH$_3$ |
| N,N-dimethylethylenediamine | —CH$_2$CH$_2$— | N(CH$_3$)$_2$ |
| N,N-ethylmethylethylenediamine | —CH$_2$CH$_2$ | N(CH$_3$)(CH$_2$CH$_3$) |

The amine functionality of these preferred resins can be either primary, secondary and/or tertiary although primary funcationality is preferred when the amine is of the formula —NHR'N(R)$_2$ and secondary and tertiary functionality is preferred when the amine is of the formula —N(R)$_2$. —N(R)$_2$ functionality is preferred to —NHR'N(R)$_2$ functionality. Especially preferred, commercial amine resins are DOWEX ® MWA-1 (comprising a macroporous, cross-linked polystyrene polymer matrix having pendant amine functionality of the formula —N(R)$_2$ wherein each R is methyl) and Amberlite ® IRA-68 (comprising a gel, cross-linked acrylic polymer matrix having pendant amine functionality).

The catalyst of this invention is prepared by loading the bimetallic cluster onto the amine resin. This loading is accomplished by a method comprising contacting in an inert liquid medium the bimetallic cluster with the amine resin. Typically, the contacting is conducted at a cluster:amine on resin mole ratio (i.e., cluster:resin mole equivalents ratio) of at least about 1:100 and preferably at least about 1:25. The maximum cluster:resin mole equivalents ratio can be varied as desired but is typically about 1:1 and preferably about 1:4.

The inert liquid medium can comprise one or more liquid solvent(s) in which the bimetallic cluster is soluble and which is inert (non-reactive) with both the method reagents and products. Aliphatic and aromatic hydrocarbons and substituted hydrocarbons are illustrative solvents and include such compounds as: hexane, benzene, toluene, xylene, o-dichlorobenzene, methylene chloride, chloroform, carbon tetrachloride, etc. The aromatic and substituted aromatic hydrocarbons are preferred with benzene and toluene especially preferred.

This method can be practiced at any temperature and pressure at which the reaction mixture of bimetallic cluster and solubilizing inert liquid medium are liquid. Convenience prefers ambient temperature and pressure, e.g., 20° C.–30° C. and atmospheric pressure. The contacting (loading) is typically conducted under an inert atmosphere, such as argon, etc. and for a sufficient period of time to load the bimetallic cluster onto the resin. This period of time will vary with the method reagents and conditions employed but with many reagents and at ambient conditions the loading is significantly commenced after about 2 hours, and is generally complete after about 12 hours. The resulting catalyst is recovered by any convenient physical separation technique, e.g., filtering.

The physical and chemical structure of the catalyst, i.e., the bimetallic cluster loaded (supported) upon the amine resin, is not fully known. However, it is known that the catalyst comprises rhodium and cobalt carbonyl attached to the amine resin. Typically, the catalyst comprises, as determined by any conventional elemental analysis method, at least about 1 weight percent, and preferably at least about 4 weight percent, rhodium (metal basis) and at least about 0.5 weight percent, and preferably at least about 2.5 weight percent, cobalt (metal basis). Resin saturation is the only limitation upon the maximum weight percent of rhodium and cobalt and the saturation levels are preferred for reasons of catalytic activity and life. Of course, saturation levels vary dependent upon the particular amine resin and bimetallic cluster employed.

The practice of this invention requires a catalytic amount of catalyst. Typically, the minimum amount of catalyst (Rh-Co metal basis) present is about 0.1 weight percent, and preferably about 0.25 weight percent, based on the weight of DCPD. Practical considerations, such as economy and convenience, are the only limitations upon the maximum amount of catalyst that can be present, although in difference to these considerations, a maximum of about 5 weight percent is preferred and a maximum of about 2 weight percent is more preferred.

Any conventional gaseous mixture of hydrogen and carbon monoxide can be here used although amounts in excess of stoichiometric hydroformylation process requirements are preferred. Typically, the minimum hydrogen:carbon monoxide ($H_2$:CO) mole ratio here used is about 1:10 and preferably about 1:1. The typical maximum $H_2$:CO mole ratio here used is about 10:1 and preferably about 2:1.

The gaseous mixture and DCPD are contacted in the presence of a catalytic amount of the catalyst at a temperature of at least about 100° C. and preferably of about 105° C. The principle limitation on the maximum temperature here used is catalyst stability. Typically the maximum temperature employed is about 125° C. and preferably about 115° C.

A pressure of least about 1,000 psig and preferably of about 1,100 psig is also here used. Practical considerations, such as economy and convenience, are the only limitations upon the maximum pressure that can be used but a maximum pressure of about 2,000 psig is preferred, with a maximum pressure of about 1,500 psig more preferred.

The reagents of this process are contacted until the hydroformylation is complete. This time will vary with the amount of catalyst employed, the composition of the DCPD (i.e., crude or purified), the temperature and pressure, etc.

This invention can be practiced either neat or in the presence of a solvent. Suitable solvents are inert to the process reagents and products at the process conditions and include both polar and nonpolar materials. Typical solvents include: aliphatic hydrocarbons, such as hexane, heptane, cyclohexane, etc.; aromatic hydrocarbons, such as benzene, toluene, xylene, etc.; and polar solvents, such as tetrahydrofuran, etc.

In one embodiment of this invention, crude DCPD is removed from a naphtha cracker and diluted with a suitable solvent, such as tetrahydrofuran or toluene, and then contacted with a gaseous mixture of hydrogen and carbon monoxide in the presence of a catalyst, such as $Rh_2Co_2(CO)_{12}$, loaded onto an amine resin, and at a pressure of at least about 1,000 psig and a temperature of at least about 100° C. until the hydroformylation is complete. Determination of complete hydroformylation is generally made by periodic sampling of the reaction mixture. When the hydroformylation is complete, substantially all the nonconjugated dienes of the crude DCPD have been selectively converted to diols, i.e., DPCD has been converted to its dimethanolic derivatives, the $C_9$ and $C_{10}$ codimers have been converted to $C_{10}$ and $C_{12}$ diols respectively, etc. The catalyst is filtered from the reaction product and the solvent subsequently stripped. The reaction product is then suitable for immediate use in the manufacture of various polyesters or polycarbonates. Thus, this specific embodiment of the invention represents an improvement in the art of hydroformylating DCPD to its dimethanolic derivatives not only because it does so in a single step, but also because it can use crude DCPD. The latter is significant because it eliminates the need to upgrade crude DCPD to purified DCPD, an operation which involves considerable capital and energy expense.

The following examples are illustrative embodiments of this invention. Unless indicated to the contrary, all parts and percentages are by weight.

SPECIFIC EMBODIMENTS

EXAMPLE 1

Crude dicyclopentadiene (1.17 g) comprising about 75 percent dicyclopentadiene (both exo and endo isomers) and between about 15 and 20 percent $C_9$–$C_{11}$ codimers (including isoprene dimer), tetrahydrofuran (2 ml), hexadecane (0.27 g, a gas chromatographic standard), and an Amberlite ® IRA-68 supported bimetallic cluster of the formula: $Rh_2Co_2(CO)_{12}$ (0.2 g, 2 percent metal loading) were charged to a reaction vessel. The vessel was subsequently heated to about 110° C. and pressurized to about 1,600 psig with a gaseous mixture of hydrogen and carbon monoxide ($H_2$:CO mole ratio of 1:1) and there maintained for about 8 hours. Subsequent gas chromatographic (GC) analysis showed the nonconjugated dienes, i.e., DCPD and the $C_9$–$C_{11}$ codimers (including isoprene codimer) to be 98 percent converted, 68.4 percent selectively converted to the corresponding dimethanolic derivatives or diols while the remainder was either monofunctionalized or hydrogenated.

EXAMPLE 2 AND 3

The procedure of Example 1 was twice repeated except that various modifications to the reaction reagents and/or conditions were made on each repetition. Each example reported greater than 98 percent conversion of the nonconjugated dienes. The individual modifications and corresponding results are tabulated below:

| Ex. | DCPD | DCPD (g) | THF[1] (ml) | HD[2] (g) | CAT.[3] (g) | TIME (hr) | TEMP (°C.) | PRES (psig) | SELECT.[4] (wt. %) |
|---|---|---|---|---|---|---|---|---|---|
| 2 | Crude | 4.98 | 30.0 | 4.0 | 1.0 | 6 | 110 | 1200 | 78.0 |

-continued

| Ex. | DCPD | DCPD (g) | THF[1] (ml) | HD[2] (g) | CAT.[3] (g) | TIME (hr) | TEMP (°C.) | PRES (psig) | SELECT.[4] (wt. %) |
|---|---|---|---|---|---|---|---|---|---|
| 3 | Purified[5] | 2.05 | 3.0 | 0.31 | 0.2 | 6 | 110 | 1200 | 81.3 |

[1] Tetrahydrofuran.
[2] Hexadecane.
[3] Catalyst (same as used in Example 1).
[4] Selectivity expressed in weight percent of the nonconjugated $C_9$–$C_{12}$ dienes converted to the corresponding diols.
[5] Purified DCPD (<5 weight percent impurities).

Although the invention has been described in detail through the preceding examples, these examples are for purpose of illustration only and many variations and modifications can be made by one skilled in the art without departing from the spirit and scope of the invention.

What is claimed is:

1. A one-step, hydroformylation process for preparing dimethanolic derivatives of dicyclopentadiene, the process comprising contacting crude dicyclopentadiene with a gaseous mixture of carbon monoxide and hydrogen at a temperature of at least 100° C. and a pressure of at least about 1,000 psig in the presence of a catalytic amount of a catalyst consisting essentially of a rhodium-cobalt carbonyl bimetallic cluster loaded onto an amine resin.

2. The process of claim 1 wherein the catalyst is prepared by loading onto an amine resin a bimetallic cluster of the formula:

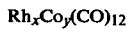

$$Rh_xCo_y(CO)_{12}$$

wherein x and y are individually integers of 1–3 with the proviso that $\Sigma(x+y)=4$.

3. The process of claim 2 wherein the catalyst comprises at least about 1 weight percent rhodium and at least about 0.5 weight percent cobalt.

4. The process of claim 3 wherein the amine resin comprises cross-linked, essentially water-insoluble swellable gel or macroporous beads.

5. The process of claim 4 wherein the amine resin comprises a cross-linked polymer matrix having pendant amine functionality of the formulae —$N(R)_2$ and/or —$NHR'N(R)_2$ wherein each R is individually hydrogen or $C_1$-$C_6$ alkyl, R' is $C_2$-$C_6$ alkylene, and the open valence is the bond that joins the functionality to the polymer matrix.

6. The process of claim 5 wherein x and y are each 2.

7. The process of claim 6 wherein the hydrogen and carbon monoxide are present in a hydrogen:carbon monoxide mole ratio of between about 1:10 and 10:1.

8. The process of claim 7 wherein the catalyst (Rh-Co metal basis) is present in an amount of at least about 0.1 weight percent based upon the weight of the dicyclopentadiene.

9. The process of claim 8 wherein the hydrogen and carbon monoxide are present in a hydrogen:carbon monoxide mole ratio of between about 1:1 and 2:1.

10. The process of claim 9 wherein the crude dicyclopentadiene comprises at least about 70 weight percent dicyclopentadiene.

* * * * *

UNITED STATES PATENT AND TRADEMARK OFFICE
CERTIFICATE OF CORRECTION

PATENT NO. : 4,262,147
DATED : April 14, 1981
INVENTOR(S) : Philip E. Garrou, George E. Hartwell It is certified that error appears in the above—identified patent and that said Letters Patent is hereby corrected as shown below:

Column 5, line 17, "difference" should read --deference--.

Column 5, line 35, insert the word --at-- after the phrase 'A pressure of'.

Column 6, line 10, "DPCD" should read --DCPD--.

Column 7, line 26, insert --about-- after the phrase 'at least'.

Signed and Sealed this

Sixth Day of October 1981

[SEAL]

Attest:

Attesting Officer

GERALD J. MOSSINGHOFF

Commissioner of Patents and Trademarks